(12) United States Patent
Budiman

(10) Patent No.: US 7,630,748 B2
(45) Date of Patent: Dec. 8, 2009

(54) METHOD AND SYSTEM FOR PROVIDING ANALYTE MONITORING

(75) Inventor: Erwin S. Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 44 days.

(21) Appl. No.: 11/552,935

(22) Filed: Oct. 25, 2006

(65) Prior Publication Data

US 2008/0119708 A1    May 22, 2008

(51) Int. Cl.
*A61B 5/05* (2006.01)
*A61B 5/00* (2006.01)

(52) U.S. Cl. .................. 600/345; 600/347; 600/365

(58) Field of Classification Search .......... 600/345, 600/347, 365
See application file for complete search history.

(56) References Cited

U.S. PATENT DOCUMENTS

| | | | |
|---|---|---|---|
| 3,581,062 A | 5/1971 | Aston |
| 3,926,760 A | 12/1975 | Allen et al. |
| 3,949,388 A | 4/1976 | Fuller |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,890,620 A | 1/1990 | Gough |

(Continued)

FOREIGN PATENT DOCUMENTS

DE    4401400    7/1995

(Continued)

OTHER PUBLICATIONS

R. Isermann and P. Balle, "Trends in the Application of Model-Based Fault Detection and Diagnosis of Technical Processes," Pergamon, Control Eng. Practice, vol. 5 No. 5, pp. 709-719, 1997, Elsevier Science Ltd, Printed in Great Britain.

(Continued)

*Primary Examiner*—Patricia C Mallari
(74) *Attorney, Agent, or Firm*—Jackson & Co., LLP

(57) ABSTRACT

Methods and apparatuses for determining an analyte value are disclosed.

7 Claims, 9 Drawing Sheets

U.S. PATENT DOCUMENTS

| | | |
|---|---|---|
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,082,550 A | 1/1992 | Rishpon et al. |
| 5,106,365 A | 4/1992 | Hernandez |
| 5,122,925 A | 6/1992 | Inpyn |
| 5,165,407 A | 11/1992 | Wilson et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,376,070 A | 12/1994 | Purvis et al. |
| 5,379,238 A | 1/1995 | Stark |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,431,160 A | 7/1995 | Wilkins |
| 5,431,921 A | 7/1995 | Thombre |
| 5,462,645 A | 10/1995 | Albery et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,609,575 A | 3/1997 | Larson et al. |
| 5,628,310 A | 5/1997 | Rao et al. |
| 5,653,239 A | 8/1997 | Pompei et al. |
| 5,665,222 A | 9/1997 | Heller et al. |
| 5,711,001 A | 1/1998 | Bussan et al. |
| 5,711,861 A | 1/1998 | Ward et al. |
| 5,772,586 A | 6/1998 | Heinonen et al. |
| 5,791,344 A | 8/1998 | Schulman et al. |
| 5,899,855 A | 5/1999 | Brown |
| 5,925,021 A | 7/1999 | Castellano et al. |
| 5,942,979 A | 8/1999 | Luppino |
| 5,957,854 A | 9/1999 | Besson et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,024,699 A | 2/2000 | Surwit et al. |
| 6,049,727 A | 4/2000 | Crothall |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,275,717 B1 | 8/2001 | Gross et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,478,736 B1 | 11/2002 | Mault |
| 6,484,046 B1 | 11/2002 | Say et al. |
| 6,514,718 B2 | 2/2003 | Heller et al. |
| 6,551,494 B1 | 4/2003 | Heller et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |

| | | | | | |
|---|---|---|---|---|---|
| 6,813,519 B2 | 11/2004 | Lebel et al. | 2004/0186365 A1 | 9/2004 | Jin et al. |
| 6,862,465 B2 | 3/2005 | Shults et al. | 2004/0193090 A1 | 9/2004 | Lebel et al. |
| 6,873,268 B2 | 3/2005 | Lebel et al. | 2004/0199059 A1 | 10/2004 | Brauker et al. |
| 6,881,551 B2 | 4/2005 | Heller et al. | 2004/0204687 A1 | 10/2004 | Mogensen et al. |
| 6,892,085 B2 | 5/2005 | McIvor et al. | 2004/0208780 A1 | 10/2004 | Faries, Jr. et al. |
| 6,895,265 B2 | 5/2005 | Silver | 2004/0225338 A1 | 11/2004 | Lebel et al. |
| 6,931,327 B2 | 8/2005 | Goode, Jr. et al. | 2004/0254433 A1 | 12/2004 | Bandis et al. |
| 6,936,006 B2 | 8/2005 | Sabra | 2004/0263354 A1 | 12/2004 | Mann et al. |
| 6,950,708 B2 | 9/2005 | Bowman, IV et al. | 2004/0267300 A1 | 12/2004 | Mace |
| 6,958,705 B2 | 10/2005 | Lebel et al. | 2005/0003470 A1 | 1/2005 | Nelson et al. |
| 6,968,294 B2 | 11/2005 | Gutta et al. | 2005/0004494 A1 | 1/2005 | Perez et al. |
| 6,971,274 B2 | 12/2005 | Olin | 2005/0010087 A1 | 1/2005 | Banet et al. |
| 6,974,437 B2 | 12/2005 | Lebel et al. | 2005/0010269 A1 | 1/2005 | Lebel et al. |
| 6,990,366 B2 | 1/2006 | Say et al. | 2005/0016276 A1 | 1/2005 | Guan et al. |
| 6,997,907 B2 | 2/2006 | Safabash et al. | 2005/0027177 A1 | 2/2005 | Shin et al. |
| 6,998,247 B2 | 2/2006 | Monfre et al. | 2005/0031689 A1 | 2/2005 | Shults et al. |
| 7,003,336 B2 | 2/2006 | Holker et al. | 2005/0043598 A1 | 2/2005 | Goode, Jr. et al. |
| 7,003,340 B2 | 2/2006 | Say et al. | 2005/0090607 A1 | 4/2005 | Tapsak et al. |
| 7,003,341 B2 | 2/2006 | Say et al. | 2005/0112169 A1 | 5/2005 | Brauker et al. |
| 7,024,245 B2 | 4/2006 | Lebel et al. | 2005/0114068 A1 | 5/2005 | Chey et al. |
| 7,041,068 B2 | 5/2006 | Freeman et al. | 2005/0131346 A1 | 6/2005 | Douglas |
| 7,052,483 B2 | 5/2006 | Wojcik | 2005/0143635 A1 | 6/2005 | Kamath et al. |
| 7,056,302 B2 | 6/2006 | Douglas | 2005/0176136 A1 | 8/2005 | Burd et al. |
| 7,074,307 B2 | 7/2006 | Simpson et al. | 2005/0182306 A1 | 8/2005 | Sloan |
| 7,081,195 B2 | 7/2006 | Simpson et al. | 2005/0187720 A1 | 8/2005 | Goode, Jr. et al. |
| 7,098,803 B2 | 8/2006 | Mann et al. | 2005/0192557 A1 | 9/2005 | Brauker et al. |
| 7,108,778 B2 | 9/2006 | Simpson et al. | 2005/0195930 A1 | 9/2005 | Spital et al. |
| 7,110,803 B2 | 9/2006 | Shults et al. | 2005/0203360 A1 | 9/2005 | Brauker et al. |
| 7,113,821 B1 | 9/2006 | Sun et al. | 2005/0239154 A1 | 10/2005 | Feldman et al. |
| 7,134,999 B2 | 11/2006 | Brauker et al. | 2005/0245795 A1 | 11/2005 | Goode, Jr. et al. |
| 7,136,689 B2 | 11/2006 | Shults et al. | 2005/0245799 A1 | 11/2005 | Brauker et al. |
| 7,171,274 B2 | 1/2007 | Starkweather et al. | 2006/0001538 A1 | 1/2006 | Kraft et al. |
| 7,190,988 B2 | 3/2007 | Say et al. | 2006/0015020 A1 | 1/2006 | Neale et al. |
| 7,192,450 B2 | 3/2007 | Brauker et al. | 2006/0015024 A1 | 1/2006 | Brister et al. |
| 7,198,606 B2 | 4/2007 | Boecker et al. | 2006/0016700 A1 | 1/2006 | Brister et al. |
| 7,226,978 B2 | 6/2007 | Tapsak et al. | 2006/0019327 A1 | 1/2006 | Brister et al. |
| 7,276,029 B2 | 10/2007 | Goode, Jr. et al. | 2006/0020186 A1 | 1/2006 | Brister et al. |
| 7,310,544 B2 | 12/2007 | Brister et al. | 2006/0020187 A1 | 1/2006 | Brister et al. |
| 2001/0041831 A1 | 11/2001 | Starkweather et al. | 2006/0020188 A1 | 1/2006 | Kamath et al. |
| 2002/0019022 A1 | 2/2002 | Dunn et al. | 2006/0020189 A1 | 1/2006 | Brister et al. |
| 2002/0042090 A1 | 4/2002 | Heller et al. | 2006/0020190 A1 | 1/2006 | Kamath et al. |
| 2002/0103499 A1 | 8/2002 | Perez et al. | 2006/0020191 A1 | 1/2006 | Brister et al. |
| 2002/0106709 A1 | 8/2002 | Potts et al. | 2006/0020192 A1 | 1/2006 | Brister et al. |
| 2002/0128594 A1 | 9/2002 | Das et al. | 2006/0036139 A1 | 2/2006 | Brister et al. |
| 2002/0161288 A1 | 10/2002 | Shin et al. | 2006/0036140 A1 | 2/2006 | Brister et al. |
| 2002/0193679 A1 | 12/2002 | Malave et al. | 2006/0036141 A1 | 2/2006 | Kamath et al. |
| 2003/0023317 A1 | 1/2003 | Brauker et al. | 2006/0036142 A1 | 2/2006 | Brister et al. |
| 2003/0032874 A1 | 2/2003 | Rhodes et al. | 2006/0036143 A1 | 2/2006 | Brister et al. |
| 2003/0042137 A1 | 3/2003 | Mao et al. | 2006/0036144 A1 | 2/2006 | Brister et al. |
| 2003/0050546 A1* | 3/2003 | Desai et al. ............... 600/347 | 2006/0036145 A1 | 2/2006 | Brister et al. |
| 2003/0065308 A1 | 4/2003 | Lebel et al. | 2006/0173444 A1 | 8/2006 | Choy et al. |
| 2003/0100821 A1 | 5/2003 | Heller et al. | 2006/0222566 A1 | 10/2006 | Brauker et al. |
| 2003/0130616 A1* | 7/2003 | Steil et al. .................. 604/66 | 2006/0226985 A1 | 10/2006 | Goodnow et al. |
| 2003/0134347 A1 | 7/2003 | Heller et al. | 2006/0247508 A1 | 11/2006 | Fennell |
| 2003/0168338 A1 | 9/2003 | Gao et al. | 2007/0027381 A1 | 2/2007 | Stafford |
| 2003/0176933 A1 | 9/2003 | Lebel et al. | 2007/0060814 A1 | 3/2007 | Stafford |
| 2003/0187338 A1 | 10/2003 | Say et al. | 2007/0073129 A1 | 3/2007 | Shah et al. |
| 2003/0199790 A1 | 10/2003 | Boecker et al. | 2007/0078320 A1 | 4/2007 | Stafford |
| 2003/0212379 A1 | 11/2003 | Bylund et al. | 2007/0078321 A1 | 4/2007 | Mazza et al. |
| 2003/0217966 A1 | 11/2003 | Tapsak et al. | 2007/0078322 A1 | 4/2007 | Stafford |
| 2004/0010207 A1 | 1/2004 | Flaherty et al. | 2007/0078323 A1 | 4/2007 | Reggiardo et al. |
| 2004/0011671 A1 | 1/2004 | Shults et al. | 2007/0106135 A1 | 5/2007 | Sloan et al. |
| 2004/0040840 A1 | 3/2004 | Mao et al. | 2007/0163880 A1 | 7/2007 | Woo et al. |
| 2004/0045879 A1 | 3/2004 | Shults et al. | 2007/0173706 A1 | 7/2007 | Neinast et al. |
| 2004/0064068 A1 | 4/2004 | DeNuzzio et al. | 2007/0203966 A1 | 8/2007 | Brauker et al. |
| 2004/0106858 A1 | 6/2004 | Say et al. | 2007/0232877 A1 | 10/2007 | He |
| 2004/0122353 A1 | 6/2004 | Shahmirian et al. | 2007/0235331 A1 | 10/2007 | Simpson et al. |
| 2004/0133164 A1 | 7/2004 | Funderburk et al. | 2007/0249922 A1 | 10/2007 | Peyser et al. |
| 2004/0138588 A1 | 7/2004 | Saikley et al. | 2008/0009692 A1 | 1/2008 | Stafford |
| 2004/0152622 A1 | 8/2004 | Keith et al. | 2008/0021666 A1 | 1/2008 | Goode, Jr. et al. |
| 2004/0171921 A1 | 9/2004 | Say et al. | | | |
| 2004/0176672 A1 | 9/2004 | Silver et al. | | | |
| 2004/0186362 A1 | 9/2004 | Brauker et al. | | | |

2008/0039702 A1 2/2008 Hayter et al.

FOREIGN PATENT DOCUMENTS

| EP | 0098592 | 1/1984 |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO 00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-2004/061420 | 7/2004 |
| WO | WO-2005/089103 | 9/2005 |
| WO | WO-2006/086423 | 8/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/056638 | 5/2007 |
| WO | WO-2007/115094 | 10/2007 |
| WO | WO-2007/120363 | 10/2007 |
| WO | WO-2007/143225 | 12/2007 |

OTHER PUBLICATIONS

R. Isermann, "Supervision, Fault-Detection and Fault-Diagnosis Methods-An Introduction," Pergamon, Control Eng. Practice, vol. 5, No. 5, pp. 639-652, 1997, Elsevier Science Ltd, Printed in Great Britain.

International Search Report and Written Opinion of the International Searching Authority for PCT Application No. PCT/US2007/082382 filed Oct. 24, 2007 to Abbott Diabetes Care, Inc., mailed Jun. 24, 2008.

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring, Chapter 4*, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

International Preliminary Report on Patentability and Written Opinion of the International Searching Authority for PCT Application No. PCT/US2007/082382 filed Oct. 24, 2007, mailed May 7, 2009.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Jungheim, K., et al., "How Rapid Does Glucose Concentration Change in Daily Life of Patients with Type 1 Diabetes?", 2002, pp. 250.

McGarraugh, G., et al., "Glucose Measurements Using Blood Extracted from the Forearm and the Finger", *TheraSense, Inc.*, 2001, 16 Pages.

\* cited by examiner

METHOD AND SYSTEM FOR PROVIDING ANALYTE MONITORING

BACKGROUND

Analyte, e.g., glucose monitoring systems including continuous and discrete monitoring systems generally include a small, lightweight battery powered and microprocessor controlled system which is configured to detect signals proportional to the corresponding measured glucose levels using an electrometer, and RF signals to transmit the collected data. One aspect of certain analyte monitoring systems include a transcutaneous or subcutaneous analyte sensor configuration which is, for example, partially mounted on the skin of a subject whose analyte level is to be monitored. The sensor cell may use a two or three-electrode (work, reference and counter electrodes) configuration driven by a controlled potential (potentiostat) analog circuit connected through a contact system.

The analyte sensor may be configured so that a portion thereof is placed under the skin of the patient so as to detect the analyte levels of the patient, and another segment of the analyte sensor that is in communication with the transmitter unit. The transmitter unit is configured to transmit the analyte levels detected by the sensor over a wireless communication link such as an RF (radio frequency) communication link to a receiver/monitor unit. The receiver/monitor unit performs data analysis, among others on the received analyte levels to generate information pertaining to the monitored analyte levels.

To obtain accurate data from the analyte sensor, calibration using capillary blood glucose measurements is necessary. Typically, blood glucose measurements are obtained using, for example, a blood glucose meter, and the measured blood glucose values are used to calibrate the sensors. Due to a lag factor between the monitored sensor data and the measured blood glucose values, an error, or signal noise such as signal dropouts, is typically introduced in calibration using the monitored data as well as in computing the displayed glucose value. While correcting for the lag factors can minimize the error due to lag in the presence of noise, in the presence of signal dropouts, such error compensation may reduce accuracy of the monitored sensor data.

In view of the foregoing, it would be desirable to have a method and system for providing noise filtering and signal dropout detection and/or compensation in data monitoring systems.

SUMMARY OF THE INVENTION

In one embodiment, a method for minimizing the effect of noise and signal dropouts in a glucose sensor including monitoring a data stream, generating a noise-filtered signal associated with the data stream, determining a presence of a signal dropout based on the noise filtered signal, and estimating a noise filtered dropout compensated signal based on the noise filtered signal and the determination of the presence of the signal dropout are disclosed.

These and other objects, features and advantages of the present invention will become more fully apparent from the following detailed description of the embodiments, the appended claims and the accompanying drawings.

DETAILED DESCRIPTION

As described in further detail below, in accordance with the various embodiments of the present invention, there is provided a method and system for providing noise filtered and/or signal dropout mitigated processes for signals in analyte monitoring systems. In particular, within the scope of the present invention, there are provided method and system for noise filtering, signal dropout detection, and signal dropout compensation to improve the accuracy of lag compensation.

Figure 1:
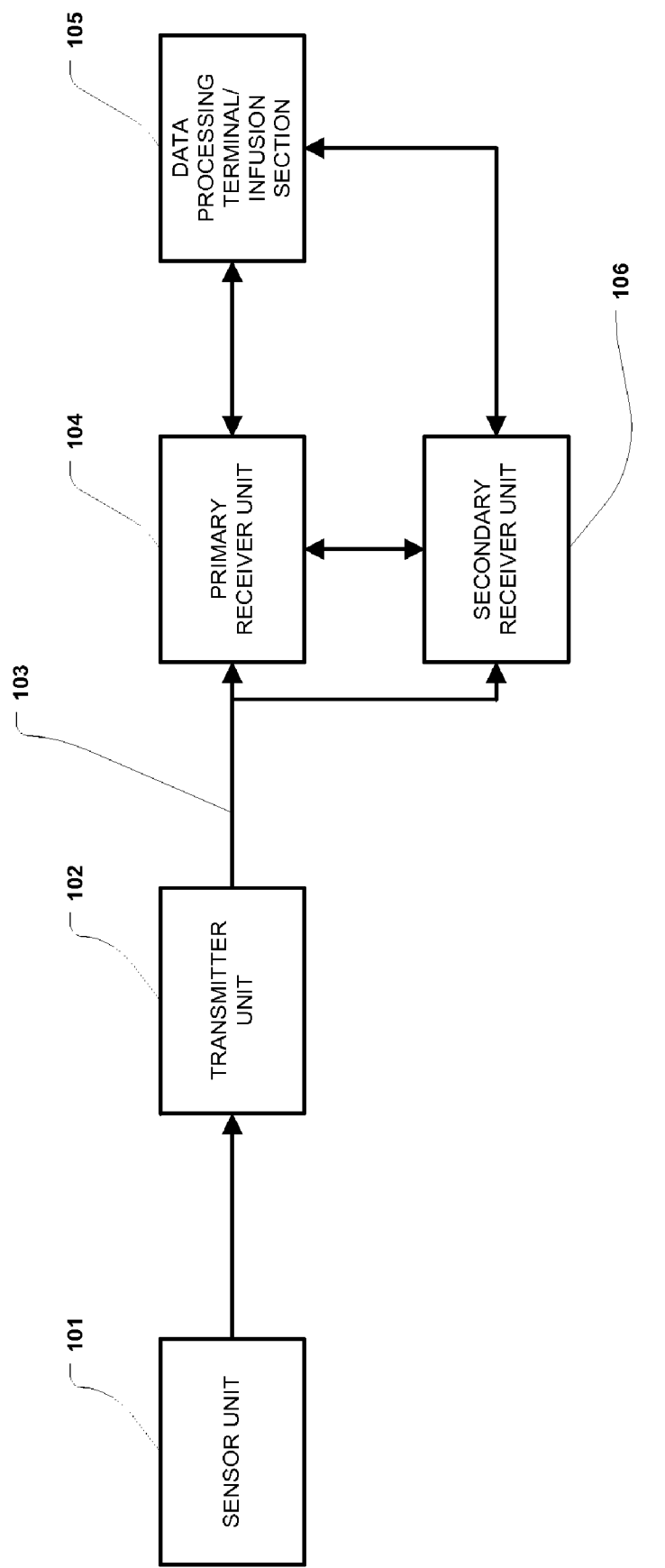
FIG. 1 illustrates a block diagram of a data monitoring and management system for practicing one or more embodiments of the present invention.

FIG. 1 illustrates a data monitoring and management system such as, for example, analyte (e.g., glucose) monitoring system 100 in accordance with one embodiment of the present invention. The subject invention is further described primarily with respect to a glucose monitoring system for convenience and such description is in no way intended to limit the scope of the invention. It is to be understood that the analyte monitoring system may be configured to monitor a variety of analytes, e.g., lactate, and the like.

Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored.

The analyte monitoring system 100 includes a sensor 101, a transmitter unit 102 coupled to the sensor 101, and a primary receiver unit 104 which is configured to communicate with the transmitter unit 102 via a communication link 103. The primary receiver unit 104 may be further configured to transmit data to a data processing terminal 105 for evaluating the data received by the primary receiver unit 104. Moreover, the data processing terminal in one embodiment may be configured to receive data directly from the transmitter unit 102 via a communication link 106 which may optionally be configured for bi-directional communication.

Also shown in FIG. 1 is a secondary receiver unit 106 which is operatively coupled to the communication link and configured to receive data transmitted from the transmitter unit 102. Moreover, as shown in the Figure, the secondary receiver unit 106 is configured to communicate with the primary receiver unit 104 as well as the data processing terminal 105. Indeed, the secondary receiver unit 106 may be configured for bi-directional wireless communication with each of the primary receiver unit 104 and the data processing terminal 105. As discussed in further detail below, in one embodiment of the present invention, the secondary receiver unit 106 may be configured to include a limited number of functions and features as compared with the primary receiver unit 104. As such, the secondary receiver unit 106 may be configured substantially in a smaller compact housing or embodied in a device such as a wrist watch, for example. Alternatively, the secondary receiver unit 106 may be configured with the same or substantially similar functionality as the primary receiver unit 104, and may be configured to be used in conjunction with a docking cradle unit for placement by bedside, for night time monitoring, and/or bi-directional communication device.

Only one sensor 101, transmitter unit 102, communication link 103, and data processing terminal 105 are shown in the embodiment of the analyte monitoring system 100 illustrated in FIG. 1. However, it will be appreciated by one of ordinary skill in the art that the analyte monitoring system 100 may include one or more sensor 101, transmitter unit 102, communication link 103, and data processing terminal 105. Moreover, within the scope of the present invention, the analyte monitoring system 100 may be a continuous monitoring system, or semi-continuous, or a discrete monitoring system. In a multi-component environment, each device is configured to be uniquely identified by each of the other devices in the system so that communication conflict is readily resolved between the various components within the analyte monitoring system 100.

In one embodiment of the present invention, the sensor 101 is physically positioned in or on the body of a user whose analyte level is being monitored. The sensor 101 may be configured to continuously sample the analyte level of the user and convert the sampled analyte level into a corresponding data signal for transmission by the transmitter unit 102. In one embodiment, the transmitter unit 102 is mounted on the sensor 101 so that both devices are positioned on the user's body. The transmitter unit 102 performs data processing such as filtering and encoding on data signals, each of which corresponds to a sampled analyte level of the user, for transmission to the primary receiver unit 104 via the communication link 103.

In one embodiment, the analyte monitoring system 100 is configured as a one-way RF communication path from the transmitter unit 102 to the primary receiver unit 104. In such embodiment, the transmitter unit 102 transmits the sampled data signals received from the sensor 101 without acknowledgement from the primary receiver unit 104 that the transmitted sampled data signals have been received. For example, the transmitter unit 102 may be configured to transmit the encoded sampled data signals at a fixed rate (e.g., at one minute intervals) after the completion of the initial power on procedure. Likewise, the primary receiver unit 104 may be configured to detect such transmitted encoded sampled data signals at predetermined time intervals. Alternatively, the analyte monitoring system 100 may be configured with a bi-directional RF (or otherwise) communication between the transmitter unit 102 and the primary receiver unit 104.

Additionally, in one aspect, the primary receiver unit 104 may include two sections. The first section is an analog interface section that is configured to communicate with the transmitter unit 102 via the communication link 103. In one embodiment, the analog interface section may include an RF receiver and an antenna for receiving and amplifying the data signals from the transmitter unit 102, which are thereafter, demodulated with a local oscillator and filtered through a band-pass filter. The second section of the primary receiver unit 104 is a data processing section which is configured to process the data signals received from the transmitter unit 102 such as by performing data decoding, error detection and correction, data clock generation, and data bit recovery.

In operation, upon completing the power-on procedure, the primary receiver unit 104 is configured to detect the presence of the transmitter unit 102 within its range based on, for example, the strength of the detected data signals received from the transmitter unit 102 or a predetermined transmitter identification information. Upon successful synchronization with the corresponding transmitter unit 102, the primary receiver unit 104 is configured to begin receiving from the transmitter unit 102 data signals corresponding to the user's detected analyte level. More specifically, the primary receiver unit 104 in one embodiment is configured to perform synchronized time hopping with the corresponding synchronized transmitter unit 102 via the communication link 103 to obtain the user's detected analyte level.

Referring again to FIG. 1, the data processing terminal 105 may include a personal computer, a portable computer such as a laptop or a handheld device (e.g., personal digital assistants (PDAs)), and the like, each of which may be configured for data communication with the receiver via a wired or a wireless connection. Additionally, the data processing terminal 105 may further be connected to a data network (not shown) for storing, retrieving and updating data corresponding to the detected analyte level of the user.

Within the scope of the present invention, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected analyte levels received from the transmitter unit 102.

Additionally, the transmitter unit 102, the primary receiver unit 104 and the data processing terminal 105 may each be configured for bi-directional wireless communication such that each of the transmitter unit 102, the primary receiver unit 104 and the data processing terminal 105 may be configured to communicate (that is, transmit data to and receive data from) with each other via the wireless communication link 103. More specifically, the data processing terminal 105 may in one embodiment be configured to receive data directly from the transmitter unit 102 via the communication link 106, where the communication link 106, as described above, may be configured for bidirectional communication.

In this embodiment, the data processing terminal 105 which may include an insulin pump, may be configured to receive the analyte signals from the transmitter unit 102, and thus, incorporate the functions of the receiver 103 including data processing for managing the patient's insulin therapy and analyte monitoring. In one embodiment, the communication link 103 may include one or more of an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements) while avoiding potential data collision and interference.

Figure 2:
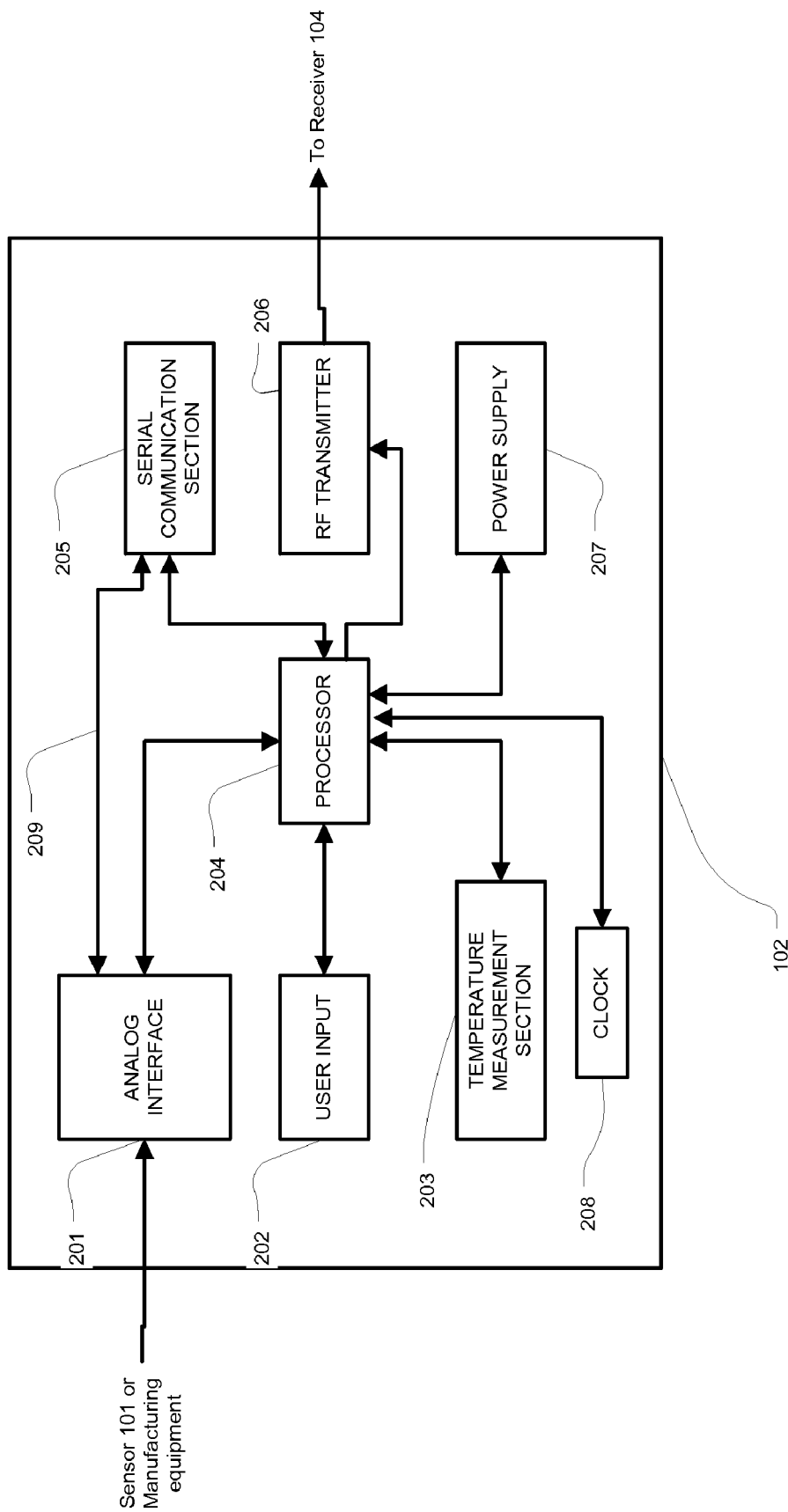
FIG. 2 is a block diagram of the transmitter unit of the data monitoring and management system shown in FIG. 1 in accordance with one embodiment of the present invention.

FIG. 2 is a block diagram of the transmitter of the data monitoring and detection system shown in FIG. 1 in accordance with one embodiment of the present invention. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). As can be seen from FIG. 2, there are provided four contacts, three of which are electrodes - work electrode (W) 210, guard contact (G) 211, reference electrode (R) 212, and counter electrode (C) 213, each operatively coupled to the analog interface 201 of the transmitter unit 102 for connection to the sensor unit 201 (FIG. 1). In one embodiment, each of the work electrode (W) 210, guard contact (G) 211, reference electrode (R) 212, and counter electrode (C) 213 may be made using a conductive material that is either printed or etched, for example, such as carbon which may be printed, or metal foil (e.g., gold) which may be etched.

Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204.

In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206. As such, in one embodiment, via the data path described above, the transmitter unit 102 is configured to transmit to the primary receiver unit 104 (FIG. 1), via the communication link 103 (FIG. 1), processed and encoded data signals received from the sensor 101 (FIG. 1). Additionally, the unidirectional communication data path between the analog interface 201 and the RF transmitter 206 discussed above allows for the configuration of the transmitter unit 102 for operation upon completion of the manufacturing process as well as for direct communication for diagnostic and testing purposes.

As discussed above, the transmitter processor 204 is configured to transmit control signals to the various sections of the transmitter unit 102 during the operation of the transmitter unit 102. In one embodiment, the transmitter processor 204 also includes a memory (not shown) for storing data such as the identification information for the transmitter unit 102, as well as the data signals received from the sensor 101. The stored information may be retrieved and processed for transmission to the primary receiver unit 104 under the control of the transmitter processor 204. Furthermore, the power supply 207 may include a commercially available battery.

The transmitter unit 102 is also configured such that the power supply section 207 is capable of providing power to the transmitter for a minimum of about three months of continuous operation after having been stored for about eighteen months in a low-power (non-operating) mode. In one embodiment, this may be achieved by the transmitter processor 204 operating in low power modes in the non-operating state, for example, drawing no more than approximately 1 μA of current. Indeed, in one embodiment, the final step during the manufacturing process of the transmitter unit 102 may place the transmitter unit 102 in the lower power, non-operating state (i.e., post-manufacture sleep mode). In this manner, the shelf life of the transmitter unit 102 may be significantly improved. Moreover, as shown in FIG. 2, while the power supply unit 207 is shown as coupled to the processor 204, and as such, the processor 204 is configured to provide control of the power supply unit 207, it should be noted that within the scope of the present invention, the power supply unit 207 is configured to provide the necessary power to each of the components of the transmitter unit 102 shown in FIG. 2.

Referring back to FIG. 2, the power supply section 207 of the transmitter unit 102 in one embodiment may include a rechargeable battery unit that may be recharged by a separate power supply recharging unit (for example, provided in the receiver unit 104) so that the transmitter unit 102 may be powered for a longer period of usage time. Moreover, in one embodiment, the transmitter unit 102 may be configured without a battery in the power supply section 207, in which case the transmitter unit 102 may be configured to receive power from an external power supply source (for example, a battery) as discussed in further detail below.

Referring yet again to FIG. 2, the temperature detection section 203 of the transmitter unit 102 is configured to monitor the temperature of the skin near the sensor insertion site. The temperature reading is used to adjust the analyte readings obtained from the analog interface 201. The RF transmitter 206 of the transmitter unit 102 may be configured for operation in the frequency band of 315 MHz to 322 MHz, for example, in the United States. Further, in one embodiment, the RF transmitter 206 is configured to modulate the carrier frequency by performing Frequency Shift Keying and Manchester encoding. In one embodiment, the data transmission rate is 19,200 symbols per second, with a minimum transmission range for communication with the primary receiver unit 104.

Referring yet again to FIG. 2, also shown is a leak detection circuit 214 coupled to the guard electrode (G) 211 and the processor 204 in the transmitter unit 102 of the data monitoring and management system 100. The leak detection circuit 214 in accordance with one embodiment of the present invention may be configured to detect leakage current in the sensor 101 to determine whether the measured sensor data are corrupt or whether the measured data from the sensor 101 is accurate.

Additional detailed description of the continuous analyte monitoring system, its various components including the functional descriptions of the transmitter are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application.

Figure 3:
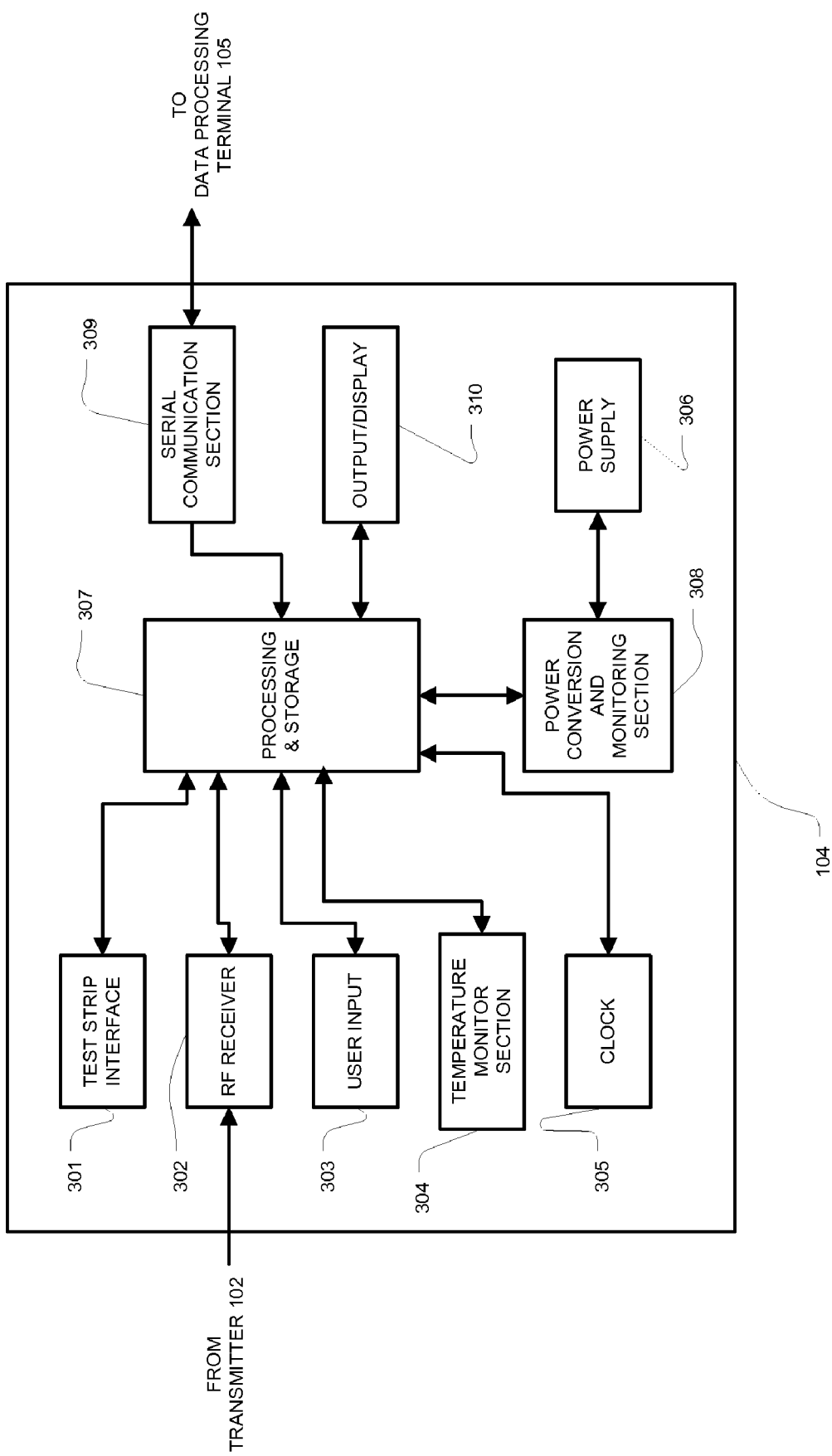
FIG. 3 is a block diagram of the receiver/monitor unit of the data monitoring and management system shown in FIG. 1 in accordance with one embodiment of the present invention.

FIG. 3 is a block diagram of the receiver/monitor unit of the data monitoring and management system shown in FIG. 1 in accordance with one embodiment of the present invention. Referring to FIG. 3, the primary receiver unit 104 includes a blood glucose test strip interface 301, an RF receiver 302, an input 303, a temperature detection section 304, and a clock 305, each of which is operatively coupled to a receiver processor 307. As can be further seen from the Figure, the primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the receiver processor 307.

In one embodiment, the test strip interface 301 includes a glucose level testing portion to receive a manual insertion of a glucose test strip, and thereby determine and display the glucose level of the test strip on the output 310 of the primary receiver unit 104. This manual testing of glucose can be used to calibrate sensor 101. The RF receiver 302 is configured to communicate, via the communication link 103 (FIG. 1) with the RF transmitter 206 of the transmitter unit 102, to receive encoded data signals from the transmitter unit 102 for, among others, signal mixing, demodulation, and other data processing. The input 303 of the primary receiver unit 104 is configured to allow the user to enter information into the primary receiver unit 104 as needed. In one aspect, the input 303 may include one or more keys of a keypad, a touch-sensitive screen, or a voice-activated input command unit. The temperature detection section 304 is configured to provide temperature information of the primary receiver unit 104 to the receiver processor 307, while the clock 305 provides, among others, real time information to the receiver processor 307.

Each of the various components of the primary receiver unit 104 shown in FIG. 3 is powered by the power supply 306 which, in one embodiment, includes a battery. Furthermore, the power conversion and monitoring section 308 is configured to monitor the power usage by the various components in the primary receiver unit 104 for effective power management and to alert the user, for example, in the event of power usage which renders the primary receiver unit 104 in sub-optimal operating conditions. An example of such sub-optimal operating condition may include, for example, operating the vibration output mode (as discussed below) for a period of time thus substantially draining the power supply 306 while the processor 307 (thus, the primary receiver unit 104) is turned on. Moreover, the power conversion and monitoring section 308 may additionally be configured to include a reverse polarity protection circuit such as a field effect transistor (FET) configured as a battery activated switch.

The serial communication section 309 in the primary receiver unit 104 is configured to provide a bi-directional communication path from the testing and/or manufacturing equipment for, among others, initialization, testing, and configuration of the primary receiver unit 104. Serial communication section 104 can also be used to upload data to a computer, such as time-stamped blood glucose data. The communication link with an external device (not shown) can be made, for example, by cable, infrared (IR) or RF link. The output 310 of the primary receiver unit 104 is configured to provide, among others, a graphical user interface (GUI) such as a liquid crystal display (LCD) for displaying information. Additionally, the output 310 may also include an integrated speaker for outputting audible signals as well as to provide vibration output as commonly found in handheld electronic devices, such as mobile telephones presently available. In a further embodiment, the primary receiver unit 104 also includes an electro-luminescent lamp configured to provide backlighting to the output 310 for output visual display in dark ambient surroundings.

Referring back to FIG. 3, the primary receiver unit 104 in one embodiment may also include a storage section such as a programmable, non-volatile memory device as part of the processor 307, or provided separately in the primary receiver unit 104, operatively coupled to the processor 307. The processor 307 is further configured to perform Manchester decoding as well as error detection and correction upon the encoded data signals received from the transmitter unit 102 via the communication link 103.

Figure 4:
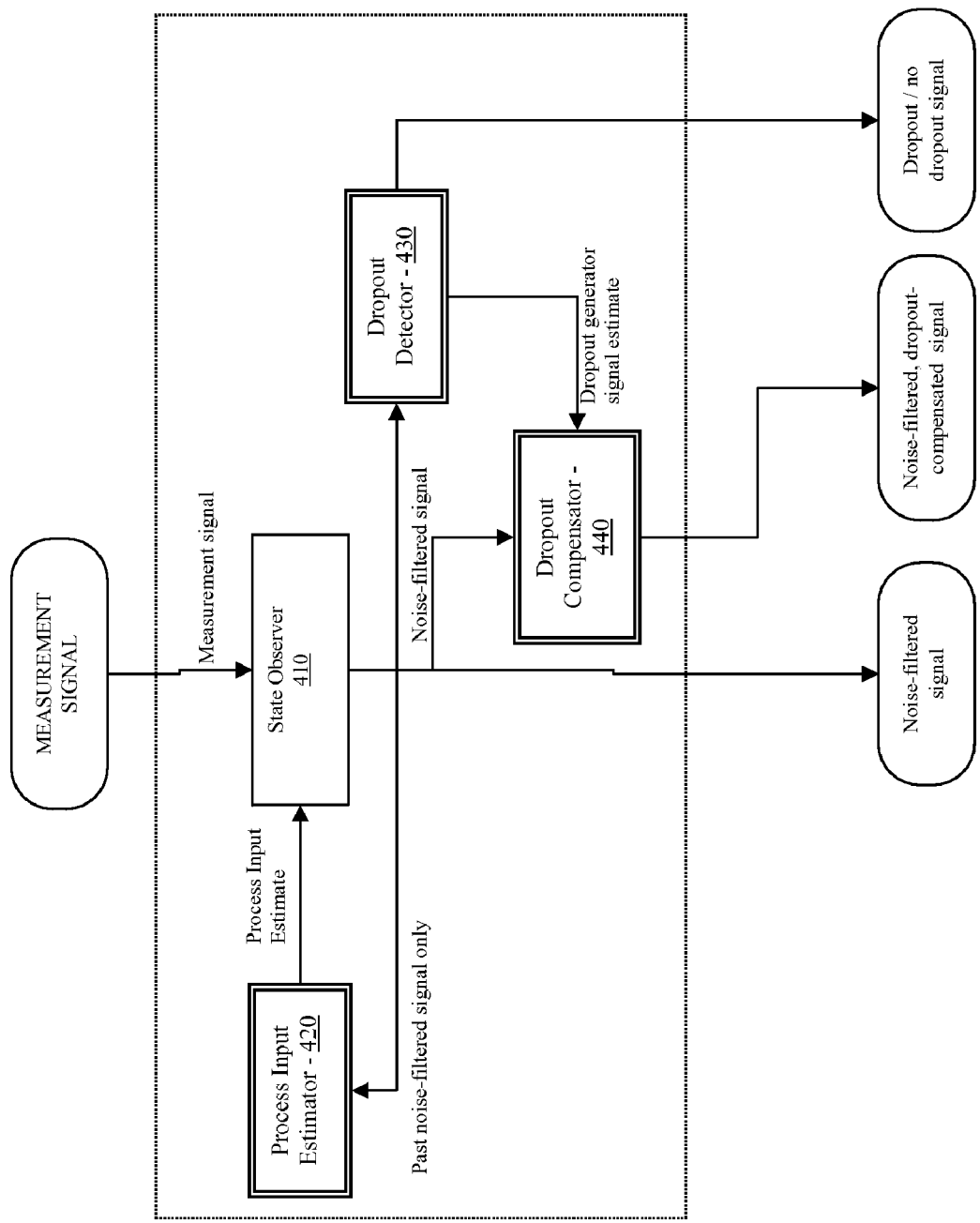
FIG. 4 is a functional diagram of the overall signal processing for noise filtering and signal dropout compensation in accordance with one embodiment of the present invention.
Figure 5:
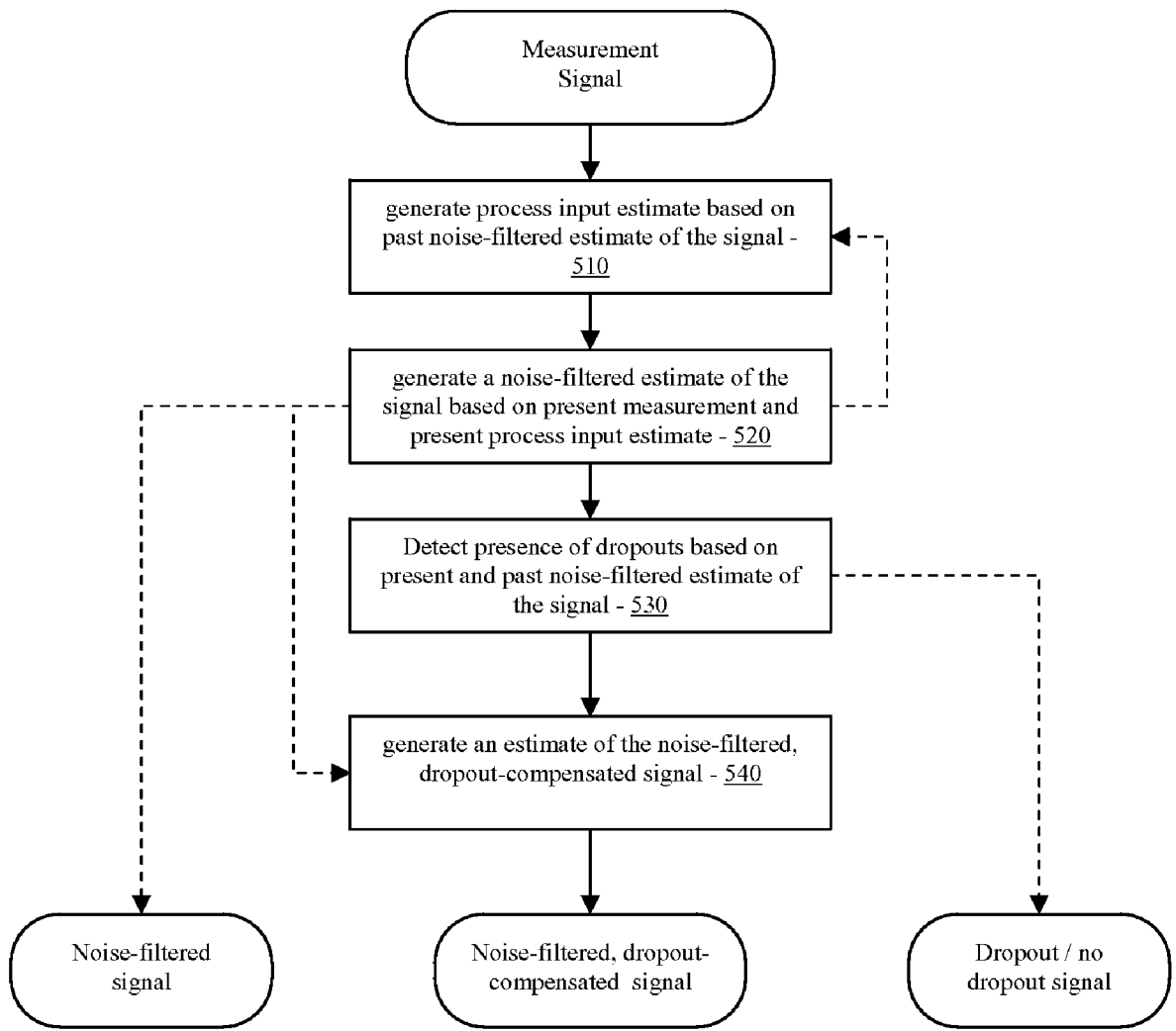
FIG. 5 is a flowchart illustrating the overall signal processing for noise filtering and signal dropout compensation in accordance with one embodiment of the present invention.

FIG. 4 is a functional diagram of the overall signal processing for noise filtering and signal dropout compensation, while FIG. 5 shows a flowchart illustrating the overall signal processing for noise filtering and signal dropout compensation in accordance with one embodiment of the present invention. Referring to the Figures, in one embodiment, signals measured are received from, for example, the analyte sensor 101 (FIG. 1) and are provided to the state observer 410 which in one embodiment may be configured to provide prior or past noise filtered estimate to a process input estimator 420.

In one embodiment, the process input estimator 420 may be configured to generate a process input estimate based on the prior or past noise filtered estimate of the received or measured signal (510), which is then provided to the state observer 410. In one aspect, and as described in further detail below in conjunction with FIG. 6, the process input estimate at a predetermined time t may be based on past noise filtered estimate of the signal.

Thereafter, in one embodiment, the state observer 410 may be configured to generate a noise filtered estimate of the measured or received signal based on the current measured or received signal and the process input estimate (520) received from the process input estimator 420. In one embodiment and as described in further detail below in conjunction with FIG. 7, using the real time process input and sensor measurement signals, a noise filtered estimate of the signal at the latest time t may be determined.

In one aspect, this routine of generating the process input estimate based on the past noise filtered estimate of the received or measured signal, and generating the noise filtered estimate of the signal based on the current received or measured signal and the current determined or generated process input estimate may be repeated for each measurement signal received, for example, from the analyte sensor 101 (FIG. 1). In this manner, in one aspect, the noise filtered signals corresponding to the measured or received sensor signals may be determined.

Referring back to FIGS. 4 and 5, in one embodiment, with the noise filtered estimate, the presence of signal dropouts are detected based on, for example, the current and past noise filtered estimate of the received or measured signal (530). More specifically, in one embodiment, a dropout detector 430 may be configured to detect signal dropouts, and thereafter, detection of signal dropouts are provided to dropout compensator 440. In one aspect, the dropout detector 430 may be configured to generate a signal or notification associated with the detection of a signal dropout (as shown in FIG .4). That is, in one embodiment and as described in further detail below in conjunction with FIG. 8, the dropout detector 430 may be configured to detect or estimate the presence or absence of signal dropouts at the predetermined time.

In one embodiment, the dropout compensator 440 may be configured to generate an estimate of the noise filtered, dropout compensated signal (540) when the signal dropout is detected (for example, by the dropout detector 430), by subtracting the estimate of the current dropout signal source from the present noise filtered estimate of the signal. In this manner, and as described in further detail below in conjunction with FIGS. 9-10, in one embodiment of the present invention, the noise filtered signal dropout mitigated or compensated signal may be generated to improve accuracy of the measured or received signal from, for example, the analyte sensor 101 (FIG. 1).

Figure 6:
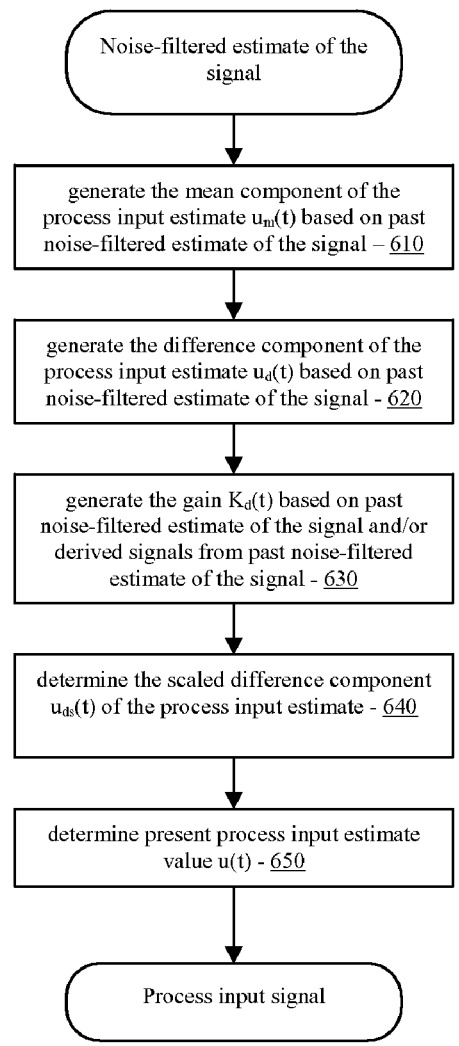
FIG. 6 is a flowchart illustrating the process input estimation in accordance with one embodiment of the present invention.

FIG. 6 is a flowchart illustrating the process input estimation in accordance with one embodiment of the present invention. Referring to FIG. 6, a mean component of the process input estimate $u_m(t)$ based on past noise filtered estimate of the signal is generated (610). For example, in one embodiment, a series of five past noise-filtered estimate of the signal, $x_i(t-5)$, $x_i(t-4)$, $x_i(t-3)$, $x_i(t-2)$, $x_i(t-1)$, the mean component of the process input estimate at time t, $u_m(t)$ may be determined by taking the unweighted average of these signals as shown by the following relationship:

$$u_m(t) = \frac{x_i(t-5) + x_i(t-4) + x_i(t-3) + x_i(t-2) + x_i(t-1)}{5} \quad (1)$$

Alternatively, the mean component of the process input estimate at time t may be determined by taking the weighted average of these signals as shown by the following relationship:

$$u_m(t) = \frac{a_5 x_i(t-5) + a_4 x_i(t-4) + a_3 x_i(t-3) + a_2 x_i(t-2) + a_1 x_i(t-1)}{a_5 + a_4 + a_3 + a_2 + a_1} \quad (2)$$

where the determination of the constants $a_1$, $a_2$, $a_3$, $a_4$, $a_5$, may be obtained based on empirical or analytical analysis of the analyte monitoring system.

In yet another embodiment, the mean component of the process input estimate at time t based on recent past data may be determined using filtering techniques, such as, but not limited to FIR filters.

Referring to FIG. 6, with the mean component of the process input estimate $u_m(t)$ based on past noise filtered estimate of the signal determined, the difference component of the process input estimate at any time t, $u_d(t)$, may be generated (620) by, for example, taking an averaged difference of a series of noise-filtered estimate of the signal from the recent past. In one aspect, an unweighted average of the last three past differences may be used in the following manner:

$$u_d(t) = \frac{(x_i(t-4) - x_i(t-3)) + (x_i(t-3) - x_i(t-2)) + (x_i(t-2) - x_i(t-1))}{3} \quad (3)$$

Within the scope of the present invention, other approaches such as the use of FIR filter to determine the proper number of recent past values of $x_i$ as well as the weighting of each difference may be used.

Referring again to FIG. 6, after determining the difference component of the process input estimate at any time t, $u_d(t)$, the difference gain at any time t, $K_d(t)$, is determined (630), for example, by using past noise-filtered estimate of the signal, $x_i$, and/or the derived signals from $x_i$. For example, in one embodiment, a band-limited rate $x_{i\_bandRate}$ and a band-limited acceleration $x_{i\_bandAcc}$ may be determined at any time t, based solely on recent past values of $x_i$. Using the knowledge of how the amount of $u_d$ would contribute to the total process input u at any time t relates to these two variables $x_{i\_bandRate}$ and $x_{i\_bandAcc}$, a functional relationship may be determined to ascertain the value of the difference gain $K_d$ at any time t.

Alternatively, a lookup table can be constructed that determines the value of the difference gain $K_d$ given the values of $x_{i\_bandRate}$ and $x_{i\_bandAcc}$ as shown below:

$$K_d = \begin{cases} 2 & \text{if } (x_{i\_bandRate} > 0) \& (x_{i\_bandAcc} > 0) \\ 1 & \text{if } (x_{i\_bandRate} > 0) \& (x_{i\_bandAcc} \leq 0) \\ 1 & \text{if } (x_{i\_bandRate} \leq 0) \& (x_{i\_bandAcc} \leq 0) \\ 0.5 & \text{if } (x_{i\_bandRate} \leq 0) \& (x_{i\_bandAcc} > 0) \end{cases} \quad (4)$$

In one aspect, the difference gain $K_d$ may be used to scale the contribution of the difference component of the process input estimate $u_d$ in the value of the process input estimate at a given time. For example, a relatively larger value of the difference gain $K_d$ may indicate a larger contribution of the difference component of the process input estimate $u_d$ in the value of the process input estimate at the particular time, and so on. In this manner, in one aspect, the lookup table may show the relationship between factors such as the band-limited rate $x_{i\_bandRate}$ and the band-limited acceleration $x_{i\_bandAcc}$ upon how much the difference component of the process input estimate $u_d$ should contribute to the process input estimate value.

Referring again to FIG. 6, with the mean component of the process input estimate $u_m(t)$, the difference component of the process input estimate at any time t, $u_d(t)$, and the difference gain at any time t, $K_d(t)$, the scaled difference component $u_{ds}(t)$ of the process input estimate may be determined (640) by multiplying the difference component of the process input estimate at any time t, $u_d(t)$ by the difference gain at any time t, $K_d(t)$. Thereafter, the scaled difference component $u_{ds}(t)$ of the process input estimate may be added to the mean component of the process input estimate $u_m(t)$ to determine the current process input estimate value u(t) (650).

Figure 7:
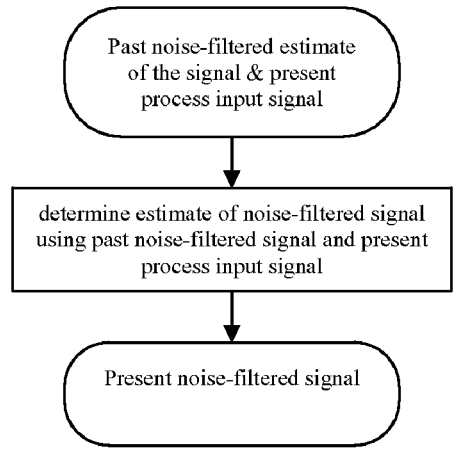
FIG. 7 is a flowchart illustrating the noise filtered estimation.

FIG. 7 is a flowchart illustrating the noise filtered estimation. Referring to FIG. 7, with an estimate of process input signal at any time t, u(t), and based on the measured signals from the analyte sensor z(t), in addition to past estimates of the noise-filtered signal $x_i(t-1)$, $x_i(t-2)$, ..., the state observer 410 (FIG. 4) may be configured to determine the estimate of noise-filtered signal at any time t, $x_i(t)$. In one aspect, the state observer 410 (FIG. 4) may be configured to reduce the contribution of noise without introducing excessive undesirable distortion based on the estimate of process input signal at any time t, u(t), and the measured signals from the sensor z(t).

Figure 8:
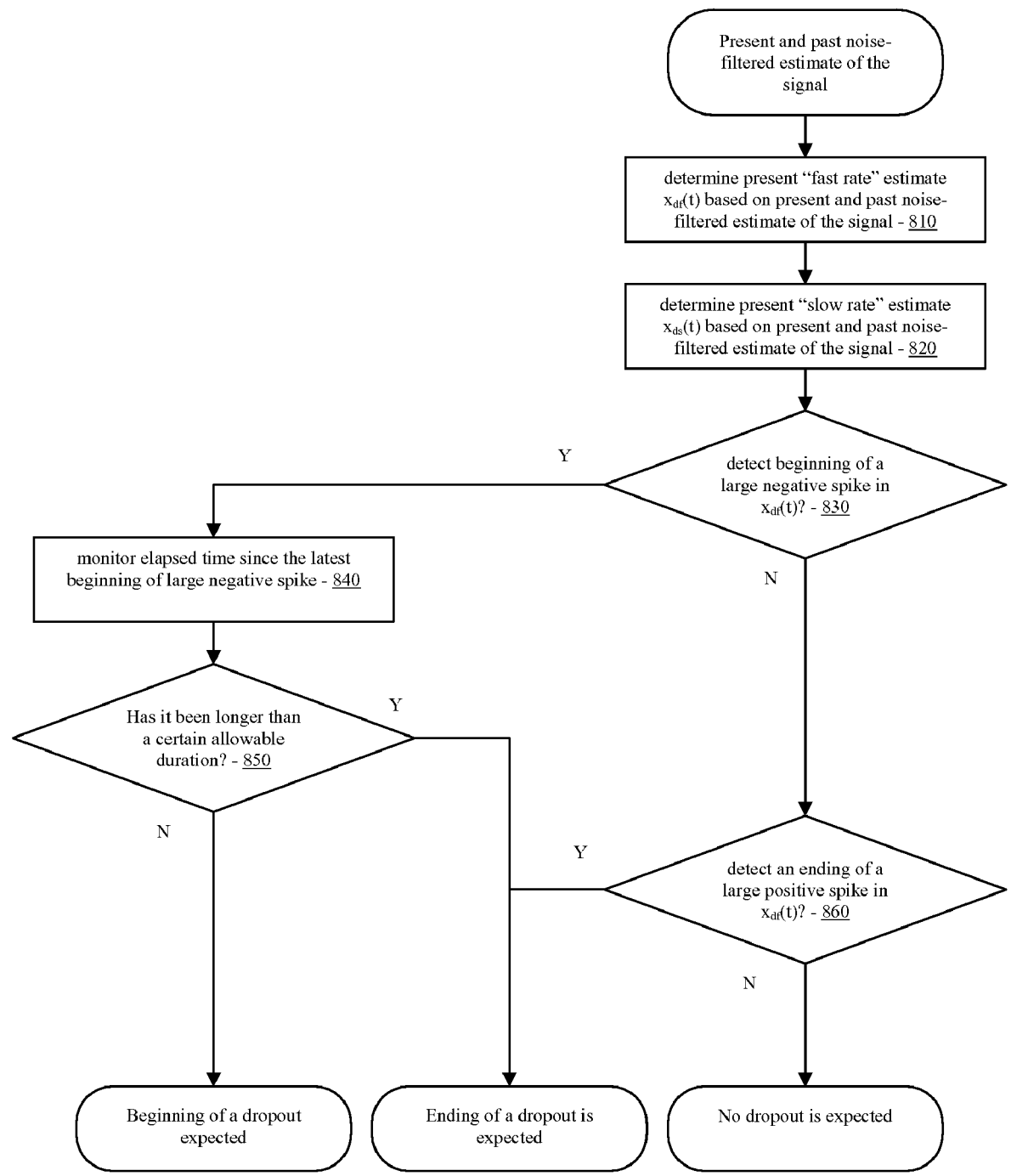
FIG. 8 is a flowchart illustrating signal dropout detection in accordance with one embodiment of the present invention.

FIG. 8 is a flowchart illustrating signal dropout detection in accordance with one embodiment of the present invention. Referring to FIG. 8, a present "fast rate" estimate $x_{df}(t)$ is determined based on present and past noise-filtered estimate of the signal (810). For example, a difference signal $x_d(t)$ may be determined based on the following expression:

$$x_d(t) = x_i(t) - x_i(t-1) \quad (5)$$

Thereafter, a fast rate may be extracted from the difference signal $x_d(t)$ by performing high pass filtering on the difference signal $x_d(t)$. In one embodiment, a discrete-time realization of a first order high pass filter function may be used to determine the present "fast rate" estimate $x_{df}(t)$:

$$x_{df}(t) = a_{hpfD} x_{df}(t-1) + x_d(t) - x_d(t-1) \quad (6)$$

where the value of $a_{hpfD}$, or the structure of the high pass filter may be determined in accordance with the suitable design configurations, for example, a value between zero and one.

Referring back to FIG. 8, after determining the "fast rate" estimate $x_{df}(t)$, a present "slow rate" estimate $x_{ds}(t)$ is determined based on present and past noise-filtered estimate of the signal (820). For example, in one embodiment, the slow rate estimate $x_{ds}(t)$ may be determined by passing the simple difference through a low-pass filter, or alternatively, by taking the difference between the simple difference and the fast difference signals as shown, for example, by the following expression:

$$x_{ds}(t)=x_d(t)-x_{df}(t) \tag{7}$$

After determining the slow rate estimate $x_{ds}(t)$, it is determined whether there is a beginning of a large negative spike in the fast rate estimate $x_{df}(t)$ (830). That is, referring to FIG. 8, the start of a signal dropout state is determined which is correlated to a spike in the fast difference. The fast difference does not generate a spike larger than a predetermined value in response to signals generated in the absence of dropouts. For example, adjusted to the units of glucose concentration, this may correspond to a fast rate in excess of −3 mg/(dL min). Although a rate of −3 mg/(dL min) or faster may be ascertained, when band pass filtered, the fast rate estimate $x_{df}(t)$ determined above does not occur in this range unless a signal dropout occurs.

Referring back to FIG. 8, if the beginning of a large negative spike in the fast rate estimate $x_{df}(t)$ is detected, then the elapsed time period from the initial occurrence of the large negative spike is monitored (840), for example, by triggering a timer or a counter so as to monitor the elapsed time since the most recent signal dropout occurrence predicted estimate. In this manner, a safety check mechanism may be provided to determine situations where a signal dropout that was anticipated to have started has lasted in an undesirably long period of dropout time period. That is, as the signal dropouts are generally intermittent in nature, it is expected that the dropout does not last beyond the order of one hour, for example, and more commonly, in the order of five to 30 minutes.

Thereafter, it is determined whether a predetermined allowable time period has elapsed (850). As shown in FIG. 8, if it is determined the allowable time period has not elapsed, then the beginning or onset of the signal dropout is estimated. On the other hand, if the predetermined allowable time period has elapsed, then the end of the signal dropout is estimated. Referring again to FIG. 8, when the beginning of a large negative spike in the fast rate estimate $x_{df}(t)$ is not detected, it is determined whether an end of a large positive spike (for example, in the order of +3 mg/(dL min)) in the fast rate estimate $x_{df}(t)$ is detected (860). If the end of the large positive spike in the fast rate estimate $x_{df}(t)$ is detected, then the end of the signal dropout is estimated. On the other hand, if the end of the large positive spike in the fast rate estimate $x_{df}(t)$ is not detected, then no signal dropout is estimated.

That is, a signal dropout is generally correlated to a large positive spike in the fast difference. Thus, in this case, the tail of the large positive spike is monitored and detected as the end of the signal dropout. In one embodiment, this maximizes the likelihood of detecting most of the instances within a signal dropout.

In this manner, in one embodiment of the present invention, the presence of signal dropout may be monitored and detected based on, for example, present and past noise filtered estimate of the signals.

Figure 9:
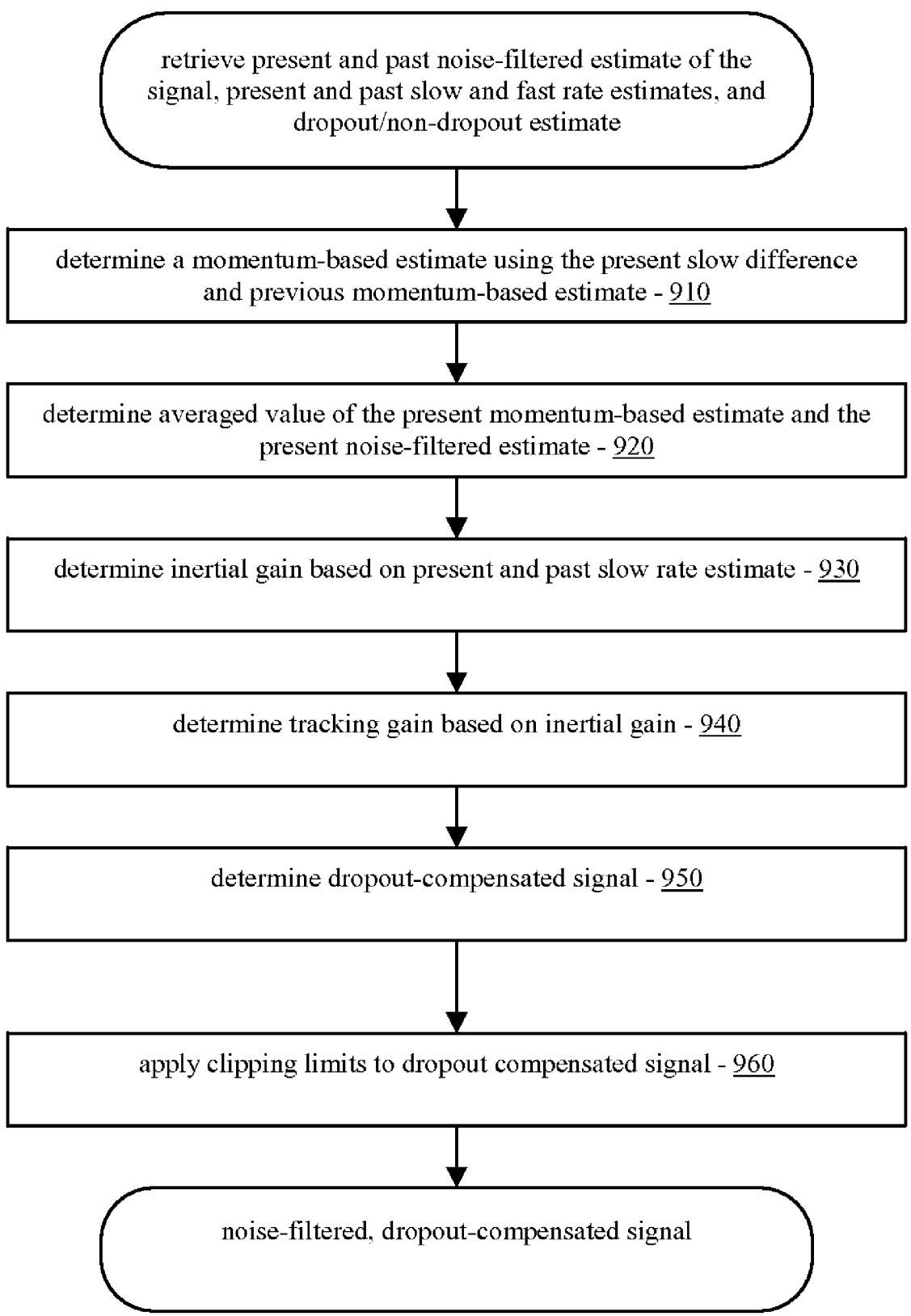
FIG. 9 is a flowchart illustrating an overall signal dropout compensation in accordance with one embodiment of the present invention.

FIG. 9 is a flowchart illustrating an overall signal dropout compensation in accordance with one embodiment of the present invention. Referring to FIG. 9, a momentum-based estimate is determined based on the present slow difference and previous momentum-based estimate (910). That is, with the present and past noise filtered estimate of the signal, the present and past slow and fast rate estimates determined as described above, and with the signal dropout detection estimation determined above, the momentum-based estimate is determined based on the present slow difference and previous momentum-based estimate. That is, in one embodiment, a momentum-based estimate may factor in a signal without dropouts as being likely to project (e.g., extrapolate) based on its past signal and its prior trend.

Referring back to FIG. 9, after determining the momentum based estimate using the present slow difference and prior momentum-based estimate, an averaged value of the present or current momentum-based estimate and the present noise filtered estimate is determined (920). Thereafter, an inertial gain based on the present and past slow rate estimate is determined (930), and which may be configured to scale the contribution of the momentum-based estimate determined using the present slow different and the previous momentum based estimate above in the final dropout compensated gain. Referring again to FIG. 9, after determining the inertial gain, a tracking gain is determined based on the inertial gain (940). In one embodiment, the determined tracking gain may be configured to scale the impact of the determined average value of the present momentum-based estimate and the present noise-filtered estimate, in the determination of the final dropout compensated signal (950) as discussed below.

Referring to FIG. 9, after determining the tracking gain, the dropout compensated signal is determined (950). In one embodiment, the dropout-compensated signal equals the noise-filtered estimate of the signal $x_i$, when no dropout is estimated. Otherwise, the dropout compensated signal may be a weighted average of the momentum-based estimate ($x_{momentum}$) as discussed above and the averaged momentum and noise-filtered estimate ($x_{average}$) also discussed above. In one aspect, the weighing factors for the weighted average of the momentum-based estimate ($x_{momentum}$) and the averaged momentum and noise-filtered estimate ($x_{average}$) may be the inertial gain $K_{inertial}$ and tracking gain $K_{tracking}$, respectively. For example, the dropout compensated signal at any time t, $x'_{dci}(t)$ in one embodiment may be determined in accordance with the following relationship:

$$x'_{dci}(t)=(K_{inertial}(t)x_{momentum}(t))+(K_{tracking}(t)x_{average}(t)) \tag{8}$$

In a further embodiment, the determination of the dropout compensated signal at any time t, $x'_{dci}(t)$ may be refined to ensure a smooth transition depending upon the underlying conditions, as described in further detail below in conjunction with FIG. 10.

Referring back to FIG. 9, after determining the dropout compensated signal, the dropout compensated signal may be clipped to be within a predetermined range (960), for example, such that the dropout compensated signal is not less than the noise-filtered signal, and further, that it is not greater than a specified safety ratio times the noise-filtered signal.

In certain cases, the resulting value of the dropout compensated signal $x'_{dci}(t)$ may fall below the noise-filtered estimate $x_i(t)$. Since by definition, a dropout is a phenomena that can only reduce the true value of a signal, the relationship (8) above for determining the dropout compensated signal may be modified by ensuring that its value never goes below $x_i(t)$ at any given time, and as shown by the following expression:

$$x_{dci}(t) = \begin{cases} x'_{dci}(t) & \text{for } x'_{dci}(t) \geq x_i(t) \\ x_i(t) & \text{for } x'_{dci}(t) < x_i(t) \end{cases} \quad (9)$$

Figure 10:
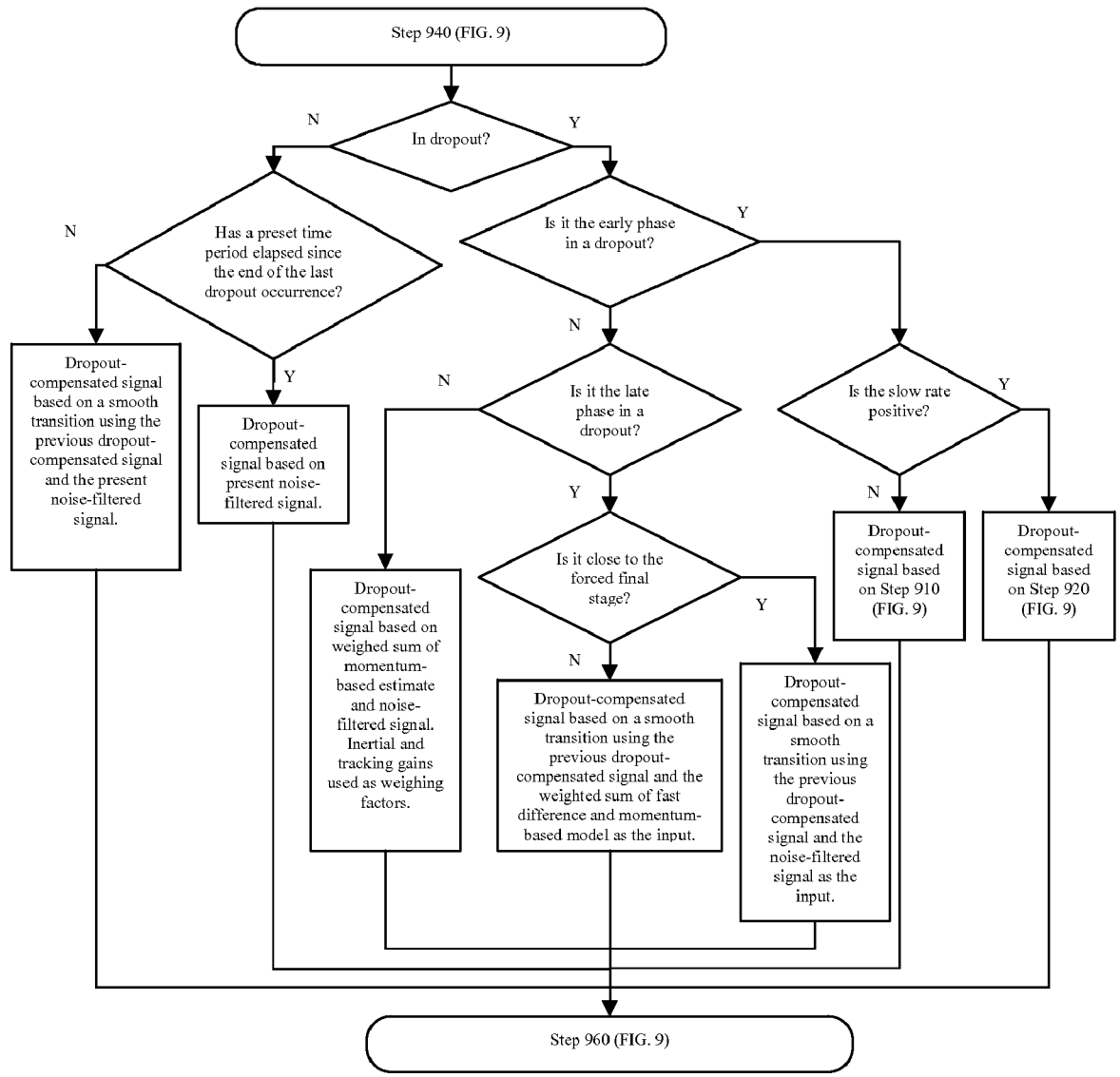
FIG. 10 is flowchart illustrating a detailed signal dropout compensation determination of FIG. 9 in accordance with one embodiment of the present invention.

FIG. 10 is flowchart illustrating a detailed signal dropout compensation determination of FIG. 9 in accordance with one embodiment of the present invention. Referring to FIG. 10, for example, in determining the drop-compensated signal, it is first determined whether signal dropout is detected. If signal dropout is not detected, then it is determined whether a preset time period has elapsed since the end of the last dropout occurrence. If it is determined that a preset time period has elapsed, then the dropout compensated signal may be based upon the present noise filtered signal. In one aspect, the preset time period may be a predetermined time period that may be considered a long period of time. On the other hand, if it is determined that the preset time period has not elapsed (that is, the end of the occurrence of a signal dropout has recently occurred), then the dropout compensated signal may be based upon a smooth transition using the previous dropout compensated signal and the present noise filtered signal.

Indeed, referring to FIG. 10, it can be seen that depending upon the determination of the timing of the signal dropout occurrence, in particular embodiments, the dropout compensated signal may be determined based on one or more factors as shown in the Figure and also described above.

Referring again to the Figures, in particular embodiments, the processings associated with the noise filtering, signal dropout detection estimation and compensation may be performed by one or more processing units of the one or more receiver unit (104, 105) the transmitter unit 102 or the data processing terminal/infusion section 105. In addition, the one or more of the transmitter unit 102, the primary receiver unit 104, secondary receiver unit 105, or the data processing terminal/infusion section 105 may also incorporate a blood glucose meter functionality, such that, the housing of the respective one or more of the transmitter unit 102, the primary receiver unit 104, secondary receiver unit 105, or the data processing terminal/infusion section 105 may include a test strip port configured to receive a blood sample for determining one or more blood glucose levels of the patient.

In a further embodiment, the one or more of the transmitter unit 102, the primary receiver unit 104, secondary receiver unit 105, or the data processing terminal/infusion section 105 may be configured to receive the blood glucose value wirelessly over a communication link from, for example, a glucose meter. In still a further embodiment, the user or patient manipulating or using the analyte monitoring system 100 (FIG. 1) may manually input the blood glucose value using, for example, a user interface (for example, a keyboard, keypad, and the like) incorporated in the one or more of the transmitter unit 102, the primary receiver unit 104, secondary receiver unit 105, or the data processing terminal/infusion section 105.

A method in one embodiment includes monitoring a data stream, generating a noise-filtered signal associated with the data stream, detecting a presence of a signal dropout based on the noise filtered signal, and estimating a noise filtered dropout compensated signal based on the noise filtered signal and the determination of the presence of the signal dropout.

In one aspect, generating the noise filtered signal may include generating one or more frequency-shaped signals based on the monitored data stream, and further, which may include high pass filtering the monitored data stream.

Also, generating the noise filtered signal in another aspect may be based on one or more previous noise filtered signals.

The method in a further embodiment may include outputting the noise filtered signal. The method in still another aspect may include outputting the noise filtered dropout compensated signal.

The method may also include generating a signal associated with detecting the presence of a signal dropout.

Moreover, the data stream in one embodiment may be associated with a monitored analyte levels of a patient.

An apparatus in another embodiment includes one or more processors, and a memory for storing instructions which, when executed by the one or more processors, causes the one or more processors to monitor a data stream, generate a noise-filtered signal associated with the data stream, detect a presence of a signal dropout based on the noise filtered signal, and estimate a noise filtered dropout compensated signal based on the noise filtered signal and the determination of the presence of the signal dropout.

The memory may be further configured for storing instructions which, when executed by the one or more processors, causes the one or more processors to generate one or more frequency-shaped signals based on the monitored data stream.

In another aspect, the memory may be further configured for storing instructions which, when executed by the one or more processors, causes the one or more processors to generate the one or more frequency shaped signals by high pass filtering the monitored data stream.

In still another aspect, the memory may be further configured for storing instructions which, when executed by the one or more processors, causes the one or more processors to generate the noise filtered signal based on one or more previous noise filtered signals.

Moreover, the memory may be further configured for storing instructions which, when executed by the one or more processors, causes the one or more processors to output the noise filtered signal.

In yet another embodiment, the memory may be further configured for storing instructions which, when executed by the one or more processors, causes the one or more processors to output the noise filtered dropout compensated signal.

Additionally, the memory may be further configured for storing instructions which, when executed by the one or more processors, causes the one or more processors to generate a signal associated with detecting the presence of a signal dropout.

A system in accordance with still another embodiment may include an analyte sensor configured to monitor an analyte of a patient, a data processing section operatively coupled to the analyte sensor, the data processing section further including one or more processors, and a memory for storing instructions which, when executed by the one or more processors, causes the one or more processors to monitor a data stream, generate a noise-filtered signal associated with the data stream, detect a presence of a signal dropout based on the noise filtered signal, and estimate a noise filtered dropout compensated signal based on the noise filtered signal and the determination of the presence of the signal dropout.

The data processing section may include a data transmission unit operatively coupled to one or more processors configured to transmit the data stream. In another aspect, the data processing section may include a data receiving unit operatively coupled to the one or more processors and configured to receive the data stream.

The analyte sensor may include a glucose sensor.

Moreover, the memory may be further configured for storing instructions which, when executed by the one or more processors, causes the one or more processors to store one or more of the data stream, the noise filtered signal, or the noise filtered dropout compensated signal.

The various processes described above including the processes performed by the receiver unit 104/105 or transmitter unit 102 in the software application execution environment in the analyte monitoring system 100 including the processes and routines described in conjunction with FIGS. 5-10, may be embodied as computer programs developed using an object oriented language that allows the modeling of complex systems with modular objects to create abstractions that are representative of real world, physical objects and their interrelationships. The software required to carry out the inventive process, which may be stored in the memory or storage unit of the receiver unit 104/105 or transmitter unit 102 may be developed by a person of ordinary skill in the art and may include one or more computer program products.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method, comprising:
   monitoring a data stream indicative of an analyte level;
   generating a noise-filtered signal associated with the data stream;
   detecting a presence of a signal dropout based on the noise filtered signal; and
   estimating, using a dropout compensator a noise filtered dropout compensated signal based on the noise filtered signal and the determination of the presence of the signal dropout;
   wherein generating the noise filtered signal is based on one or more previous noise filtered signals.

2. The method of claim 1 wherein generating the noise filtered signal includes generating one or more frequency-shaped signals based on the monitored data stream.

3. The method of claim 2 wherein generating the one or more frequency shaped signals include high pass filtering the monitored data stream.

4. The method of claim 1 further including outputting the noise filtered signal.

5. The method of claim 1 further including outputting the noise filtered dropout compensated signal.

6. The method of claim 1 further including generating a signal associated with detecting the presence of a signal dropout.

7. The method of claim 1 wherein the data stream is associated with a monitored analyte levels of a patient.

* * * * *

UNITED STATES PATENT AND TRADEMARK OFFICE
CERTIFICATE OF CORRECTION

PATENT NO. : 7,630,748 B2
APPLICATION NO. : 11/552935
DATED : December 8, 2009
INVENTOR(S) : Erwin S. Budiman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 88 days.

Signed and Sealed this

Second Day of November, 2010

David J. Kappos
*Director of the United States Patent and Trademark Office*